United States Patent
Luhman

(10) Patent No.: US 9,427,414 B2
(45) Date of Patent: *Aug. 30, 2016

(54) METHOD AND COMPOSITION FOR ENHANCING MILK PRODUCTION

(71) Applicant: LAND O'LAKES, INC., Arden Hills, MN (US)

(72) Inventor: Cindie M. Luhman, Webster Groves, MO (US)

(73) Assignee: LAND O'LAKES, INC., Arden Hills, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,070

(22) Filed: Jan. 7, 2016

(65) Prior Publication Data

US 2016/0193158 A1 Jul. 7, 2016

Related U.S. Application Data

(63) Continuation of application No. 14/627,866, filed on Feb. 20, 2015, now Pat. No. 9,241,914, which is a continuation of application No. 13/863,125, filed on Apr. 15, 2013, now Pat. No. 8,980,306, which is a continuation of application No. 11/256,495, filed on Oct. 21, 2005, now Pat. No. 8,440,218, which is a continuation of application No. 10/147,551, filed on May 17, 2002, now Pat. No. 7,037,518, which is a continuation of application No. 09/338,314, filed on Jun. 22, 1999, now Pat. No. 6,440,447.

(51) Int. Cl.
*A23K 1/18* (2006.01)
*A61K 31/047* (2006.01)
*A61K 47/46* (2006.01)

(52) U.S. Cl.
CPC ............. *A61K 31/047* (2013.01); *A61K 47/46* (2013.01)

(58) Field of Classification Search
None
See application file for complete search history.

(56) References Cited

U.S. PATENT DOCUMENTS

| | | |
|---|---|---|
| 2,876,157 A | 3/1959 | Selden |
| 3,338,718 A | 8/1967 | Olson et al. |
| 3,794,732 A | 2/1974 | Raun |
| 3,857,971 A | 12/1974 | Abdo et al. |
| 3,928,571 A | 12/1975 | Raun |
| 3,956,482 A | 5/1976 | Hahn et al. |
| 3,959,493 A | 5/1976 | Baalsrud et al. |
| 4,127,676 A | 11/1978 | Merensalmi |
| 4,181,709 A | 1/1980 | Dannelly |
| 4,289,784 A | 9/1981 | Bochis et al. |
| 4,376,790 A | 3/1983 | Ames |
| 4,704,276 A | 11/1987 | Kantor |
| 4,735,735 A | 4/1988 | Borggrefe et al. |
| 4,735,809 A | 4/1988 | Donovan et al. |
| 4,876,097 A | 10/1989 | Autant et al. |
| 4,996,067 A | 2/1991 | Kobayashi et al. |
| 5,021,241 A | 6/1991 | Yamahira et al. |
| 5,081,146 A | 1/1992 | Fontenot et al. |
| 5,137,735 A | 8/1992 | Bignon |
| 5,139,777 A | 8/1992 | Ott et al. |
| 5,145,695 A | 9/1992 | Smith et al. |
| 5,190,775 A | 3/1993 | Klose |
| 5,219,596 A | 6/1993 | Smith et al. |
| 5,236,718 A | 8/1993 | Huchette |
| 5,244,669 A | 9/1993 | Satoh et al. |
| 5,252,561 A | 10/1993 | Hornykiewytsch et al. |
| 5,380,525 A | 1/1995 | Leedle et al. |
| 5,474,785 A | 12/1995 | Wright et al. |
| 5,496,571 A | 3/1996 | Blagdon et al. |
| 5,503,112 A | 4/1996 | Luhman et al. |
| 5,518,730 A | 5/1996 | Fuisz |
| 5,529,793 A | 6/1996 | Garner et al. |
| 5,547,686 A | 8/1996 | Jenkins |
| 5,560,919 A | 10/1996 | Morikawa et al. |
| 5,585,134 A | 12/1996 | Cummings et al. |
| 5,660,852 A | 8/1997 | McKeown et al. |
| 5,707,617 A | 1/1998 | Conrad et al. |
| 5,741,506 A | 4/1998 | Bauchart et al. |
| 5,767,080 A | 6/1998 | Beck |
| 5,807,594 A | 9/1998 | King et al. |
| 5,843,498 A | 12/1998 | Takahashi |
| 5,858,424 A | 1/1999 | Virkki et al. |
| 5,874,103 A | 2/1999 | Moore et al. |
| 5,906,842 A | 5/1999 | Sato et al. |
| 5,958,464 A | 9/1999 | Register |
| 6,106,871 A | 8/2000 | Miller |
| 6,217,915 B1 | 4/2001 | Luchansky et al. |

(Continued)

FOREIGN PATENT DOCUMENTS

| | | |
|---|---|---|
| CA | 600707 | 5/1960 |
| CA | 645019 | 7/1962 |

(Continued)

OTHER PUBLICATIONS

Christensen et al. "Effect of Method of Delivery of Propylene Glycol on Plasma Metabolites of Feed-Restricted Cattle," *J. of Dairy Science*, vol. 80, pp. 563-564 (1997).

Ensminger. *Feeds & Nutrition*, pp. 520, 526, 567 (1978).

Ensminger. "Challenge Feeding," *Animal Science*, pp. 725-726, (1977).

Khalili et. al. "The Effects of Added Glycerol or Unprotected Free Fatty Acids or a Combination of the Two on Silage Intake, Milk Production, Rumen Fermentation and Diet Digestibility in Cows Given Grass Silage Based Diets," *Agricultural Food Science in Finland*; vol. 6; Nos. 5-6; pp. 349-362 (May 1997).

(Continued)

*Primary Examiner* — Jeffrey T Palenik
(74) *Attorney, Agent, or Firm* — Dorsey & Whitney LLP; Bridget M. Hayden, Esq.

(57) ABSTRACT

The present invention concerns a method of enhancing milk production by a ruminant that includes providing a feed that contains sorbitol and at least one additional feed component, and orally feeding the feed to the ruminant, the ruminant ingesting about 100 grams, or less, of sorbitol per day.

7 Claims, 1 Drawing Sheet

(56) References Cited

U.S. PATENT DOCUMENTS

| | | |
|---|---|---|
| 6,229,031 B1 | 5/2001 | Strohmaier et al. |
| 6,306,427 B1 | 10/2001 | Annonier et al. |
| 6,326,051 B1 | 12/2001 | Nakasugi et al. |
| 6,440,447 B1 | 8/2002 | Luhman |
| 6,521,249 B2 | 2/2003 | Block et al. |
| 6,866,861 B1 | 3/2005 | Luhman |
| 7,037,518 B2 | 5/2006 | Luhman |
| 7,371,401 B2 | 5/2008 | Miller |
| 8,110,214 B2 | 2/2012 | Porter et al. |
| 8,591,937 B2 | 11/2013 | Porter et al. |
| 2002/0127259 A1 | 9/2002 | Orthoefer |
| 2003/0072788 A1 | 4/2003 | Luhman |
| 2004/0142065 A1 | 7/2004 | de Rodas et al. |
| 2005/0142168 A1 | 6/2005 | Porter et al. |
| 2006/0057274 A1 | 3/2006 | Miller |
| 2006/0088576 A1 | 4/2006 | Luhman |
| 2008/0146520 A1 | 6/2008 | Block et al. |
| 2009/0028995 A1 | 1/2009 | Miller |
| 2012/0195998 A1 | 8/2012 | Porter et al. |

FOREIGN PATENT DOCUMENTS

| | | |
|---|---|---|
| CA | 2330091 | 7/2002 |
| EP | 0998853 B1 | 5/2000 |
| FR | 2469131 | 5/1981 |
| GB | 838766 | 6/1960 |
| GB | 2159690 | 11/1985 |
| WO | WO 93/21782 | 11/1993 |
| WO | WO 97/33488 A1 | 9/1997 |
| WO | WO 00/78160 | 12/2000 |
| WO | WO 01/67879 | 9/2001 |
| WO | WO 03/037102 A2 | 5/2003 |
| WO | WO 03/045401 A1 | 6/2003 |
| WO | WO 03/090696 A2 | 11/2003 |

OTHER PUBLICATIONS

Remond et al. "Effects of Feeding Sorbitol on Milk Yield and Blood Characteristics in Dairy Cows in Early Lactation", or "Effet De L'addition De Sorbitol A La Ration Des Vaches Laitieres En Debut De Lactation Sur Leurs Performances et Sur Quelques Parametres Sanguins"; *Reprod Nutr. Dev.* 26 (1 B); pp. 365-366 (1986).

Makinen et al. "A Polyol Mixture in the Diet of Dairy Cows," *Nutrition Reports International*, vol. 23, No. 6, pp. 1077-1088 (Jun. 1981).

Choung et al. "The Effects of Abomasal Infusions of Casein or Soya-Bean-Protein Isolate on the Milk Production of Dairy Cows in Mid-Lactation," *British Journal of Nutrition*, vol. 69, pp. 103-115 (1993).

Oldick et al. "Abomasal Infusion of Glucose and Fat-Effect on Digestion, Production, and Ovarian and Uterine Functions of Cows," (abstract), *J. Dairy Sci,.* vol. 80, pp. 1315-1328 (Jul. 1997), published at: <http://www.aces.uiuc.edu/-gregm/adsa/jds/abs/97/Jul97/ab1315.html>.

Istasse et al. "The Effects of Abomasal Infusions of Casein or Glucose on Milk Yield and on Some Blood Constituents of Diary Cows in Early and Late Lactation" (Abstract), *Journal of British Society of Animal Production*, pp. 538-539. (1984).

Oldham et al. "Milk Production in Cows Infused Abomasally with Casein, Glucose or Aspartic and Glutamic Acids Early in Lactation" (Abstract), *Proceedings of the Nutrition Society*, p. 65A, vol. 43 (1984).

Lister et al. "Effects of Intraruminal Administration of Polyol to Sheep," *J. Sci. Food Agric.*, vol. 35, pp. 21-28 (1984).

Sauer et al. "Propylene Glycol and Glycerol as a Feed Additive for Lactating Dairy Cows: *An Evaluation of Blood Metabolite Parameters,*" *Canadian Journal of Animal Science*; vol. 53, pp. 265-271, 1973.

Fisher et al. "Effects of Propylene Glycol or Glycerol Supplementation of the Diet of Dairy Cows on Feed Intake, Milk Yield and Composition, and Incidence of Ketosis," *Canadian Journal of Animal Science*, vol. 53, No. 2; pp. 289-296 (1973).

Boyd et al Effects of the Addition of Direct-Fed Microbials & Glycerol to the Diet—J. of Dairy Sci. 94: pp. 4616-4622, Nov. 3, 2010.

Lundeen in Feedstuffs, Jul. 11, 2005 vol. 77 #28 Supplements Aid Dairy Cows.

Roquette, "Significance of Adding Neosorb Sorbitol to the Feed Ration of Calves and Young Bulls", pp. 1-24, 1988.

Figure 1. Dry matter intake of cows fed control or sorbitol.
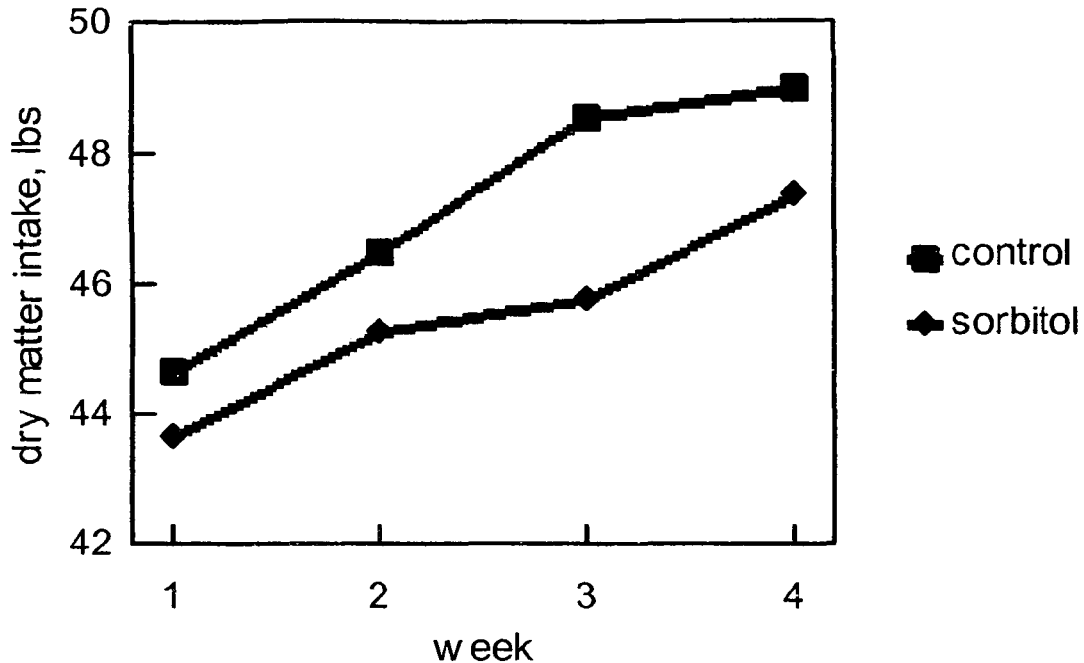
Figure 2. Milk production of cows fed control or sorbitol.
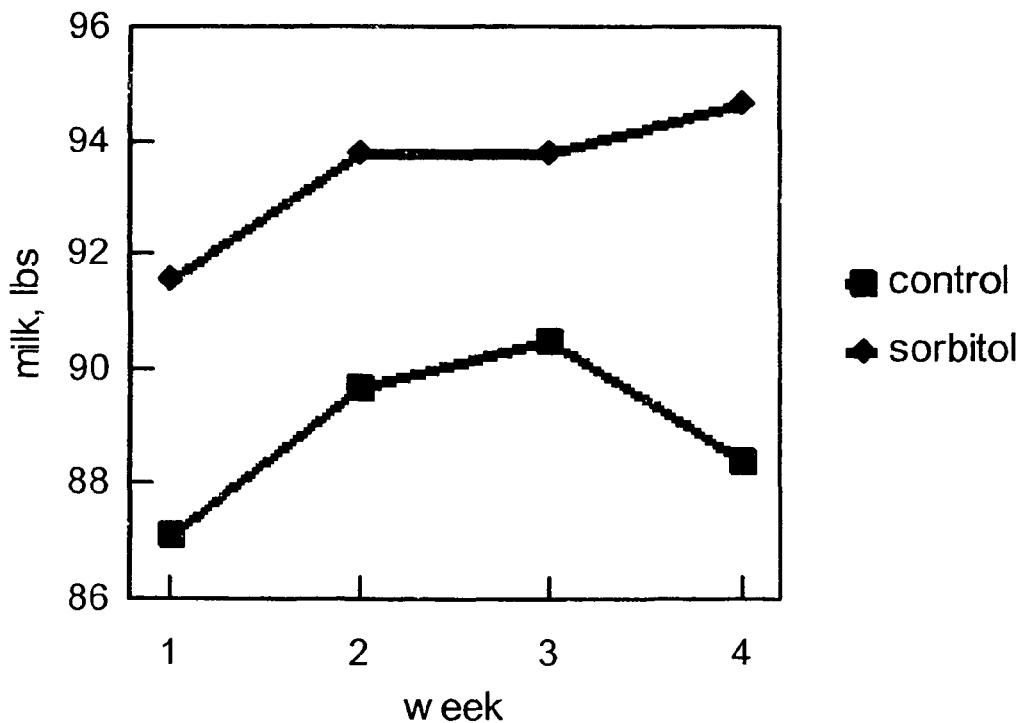

METHOD AND COMPOSITION FOR ENHANCING MILK PRODUCTION

CROSS-REFERENCE TO RELATED APPLICATION(S)

This application is a continuation of U.S. application Ser. No. 14/627,866 filed on Feb. 20, 2015, issued as U.S. Pat. No. 9,241,914 on Jan. 26, 2016, which is a continuation of U.S. application Ser. No. 13/863,125 filed on Apr. 15, 2013, issued as U.S. Pat. No. 8,980,306 on Mar. 17, 2015, which is a continuation of U.S. application Ser. No. 11/256,495 filed on Oct. 21, 2005, issued as U.S. Pat. No. 8,440,218 on May 14, 2013, which is a continuation of U.S. application Ser. No. 10/147,551 filed on May 17, 2002, issued as U.S. Pat. No. 7,037,518 on May 2, 2006, which is a continuation of U.S. application Ser. No. 09/338,314 filed on Jun. 22, 1999, issued as U.S. Pat. No. 6,440,447 on Aug. 27, 2002, the contents of all of which are herein incorporated by reference in its entirety.

BACKGROUND OF THE INVENTION

The present invention generally relates to a method and composition for enhancing milk production. More particularly, the present invention relates to a method and composition for enhancing milk production by ruminants.

Milk producers are continually looking for new compositions and methods that permit a selective increase in the amount of milk produced by ruminants. A number of advances have been made over the years in incrementally increasing milk production by ruminants. For example, various changes in the ingredient composition of ruminant feed have been made in attempts to coax ruminants into increasing the amount of feed intake, increasing the amount of water intake, and/or adding particular feed components that are thought to aid in increasing the amount of milk produced by ruminants.

Additionally, some efforts have focused upon modifying the feed to cause digestion of particular feed components in particular stomach components of the ruminant. For example, techniques exist for making certain feed components or feed additives, such as certain proteins and amino acids, rumen-inert to prevent these components from being digested in the rumen and to consequently permit digestion of these select components in stomach components other than the rumen, such as in the abomasum. Complicating matters further, care must be taken to assure that the particular feeding change does not cause health problems in the ruminant, such as rumina! keratosis, abomasal displacement, or laminitis.

Though the various ruminant feeding techniques that have been proposed and/or practiced over the years have enhanced the overall knowledge base with respect to ruminant feeding, these techniques have not adequately addressed the problem of how to most economically, efficiently, and effectively increase the amount of milk produced by ruminants. Therefore, a need still exists for an improved method and composition for feeding ruminants that enhances the amount of milk produced by the ruminants.

SUMMARY OF THE INVENTION

The present invention includes a method of enhancing milk production by a ruminant. The method includes providing a feed that contains sorbitol and at least one additional feed component, and orally feeding the feed to the ruminant, the ruminant ingesting about 100 grams, or less, of sorbitol per day. The present invention further includes a feed material and a method of feeding a ruminant.

BRIEF DESCRIPTION OF THE DRAWINGS

FIG. 1 is a graph depicting differences in dry matter intake in lactating cows that are fed a control ration versus lactating cows that are fed the control ration, along with sorbitol, in accordance with the present invention.

FIG. 2 is a graph depicting differences in the amount of milk production by lactating cows fed the control ration versus lactating cows fed the control ration, along with sorbitol, in accordance with the present invention.

DETAILED DESCRIPTION

The present invention includes both a method and a feed composition for enhancing the amount of milk production by ruminants. The method of the present invention entails feeding ruminants the feed composition that includes at least one sugar alcohol, where the feed composition is orally fed to the ruminant.

It has been discovered that if a sugar alcohol is orally fed to a ruminant, even at low rates, such as about one hundred grams of sorbitol per day per ruminant, the amount of milk produced by the ruminant is surprisingly increased. This is a surprising result, since it has traditionally been thought that orally ingested sugar alcohol would be substantially, if not predominantly, digested in the rumen of the ruminants and would consequently cause negligible, if any, increases in milk production by the ruminants. However, in accordance with the present invention, it has been discovered that as much as at least about 50 weight percent of the sugar alcohol, based upon the total amount of sugar alcohol orally fed to the ruminant, passes through the rumen of the ruminant and into the abomasum of the ruminant within about six to about eight hours after the sugar alcohol enters the rumen, when using sorbitol as the sugar alcohol. It is believed that the makeup of the feed composition administered in accordance with the present invention helps to minimize the residence time, and consequently digestion, of the sorbitol in the rumen. Therefore, the fibrous content of the feed composition is preferably reduced, relative to the fibrous content of existing traditional ruminant feeds, to aid in minimizing the residence time of sorbitol in the rumen.

As used herein, the term "ruminant" means an even-toed hoofed animal which has a complex 3- or 4-chamber stomach and which typically rechews what it has previously swallowed. Some non-exhaustive examples of ruminants include cattle, sheep, goats, oxen, musk ox, llamas, alpacas, guanicos, deer, bison, antelopes, camels, and giraffes. The digestive tract of a cow, one example of the ruminant that may be fed in accordance with the present invention, includes a stomach that has four sections: a rumen, a reticulum, an omasum, and an abomasum. The four sections of the stomach may affect digestion of a component passing through the stomach because each section of the stomach serves a different function in the digestive process. In the rumen, food is mixed with saliva and then churned in a coordinated motion. The food mixture undergoes some fermentation and bacterial digestion in the rumen. The mixture of food and saliva then passes to the reticulum where the mixture is formed into a cud that can be regurgitated. After thorough chewing of the regurgitated cud, the cud is reswallowed and then passes from the rumen through the reticulum and into the omasum, if particle size restrictions are satisfied. While in the omasum, the mixture is additionally mixed to maintain it in a homogenous state and to remove excess fluid. Then, the homogenous mixture is passed from the omasum to the abomasum, where gastric digestion occurs.

As explained above, the feed composition administered in accordance with the present invention includes, or is orally fed to the ruminants along with, at least one sugar alcohol. As used herein, sugar alcohol is defined as a polyhydric alcohol formed by the reduction of the carbonyl group of a sugar to a hydroxyl group, with no more than one hydroxy group being attached to any one carbon atom of the sugar alcohol. The sugar alcohol that is included as part of the feed composition or that is added to the feed composition in accordance with the present invention may take any form. For example, the sugar alcohol may be crystalline, in the form of a syrup, or in the form of an aqueous mixture of water and crystalline sugar alcohol and/or water and sugar alcohol syrup.

One preferred example of the sugar alcohol that may be used in practicing the present invention is sorbitol. Some other examples of sugar alcohols that may be used in practicing the present invention include adonitol; allitol; alcritol (D-altritol, L-altritol, and D,L altritol); arabinitol (D-arabinitol, L-arabinitol, and D,L arabinitol); dulcitol (a.k.a galactitol); erythritol; galaxitol; glucitol (D-glucitol, L-glucitol, and D,L glucitol); glycerol; iditol (D-iditol and L-iditol); inositol; isomalt; lactitol; maltitol; mannitol (D-mannitol, L-mannitol, and D,L mannitol); perseitol; ribitol; rhamnitol; threitol (D-threitol, L-threitol, and D,L threitol); and xylitol. These sugar alcohols may be provided in any combination as part of, or along with, the feed composition. Preferably, however, only one of these sugar alcohols is included in, or along with, any particular batch of the feed composition that is orally fed to the ruminants.

In addition to, or along with, the sugar alcohol, the feed composition that is orally fed to the ruminant may include any other conventional ruminant feed component that is capable of being blended with the sugar alcohol as part of the feed composition or that is capable of being combined with the feed composition of the present invention, so long as the feed components do not hinder abomasal or intestinal function and are not otherwise harmful to the ruminant. Some nonexhaustive examples of such feed components that may be included as part of the feed composition of the present invention include water, beans, grains, bean- or grain-based oils, bean- or grain-based meals, beari- or grain-based haylage or silage, bean- or grain-based syrups, fatty acids, commercially available formula feeds, and mixtures thereof. Some examples of suitable formula feeds include Peak Plus® 37 formula feed, Fresh Tran Plus® formula feed, and Condition Plus® formula feed that are each available from Land O'Lakes, Inc. of Arden Hills, Minn., and QLf® 4-19 formula feed that is available from Quality Liquid Feeds, Inc. of Dodgeville, Wis.

One preferred formulation the feed composition includes about 10 to about 15 weight percent alfalfa haylage, about 10 to about 15 weight percent alfalfa hay, about 25 to about 30 weight percent corn silage, about 15 to about 20 weight percent cracked corn, about 5 to about 10 weight percent Peak Plus® 37 formula feed, about 8 to about 13 weight percent Fresh Tran Plus® about 3 to about 6 weight percent Condition Plus®, and about 3 to about 6 weight percent QLF® 4-19 formula feed, based upon the dry matter weight of the feed composition. This preferred form of the feed composition permits at least as much as about 50 weight percent of the sorbitol, based upon the total amount of sorbitol orally fed to the ruminant, to pass through the rumen of the ruminant and into the abomasum of the ruminant within about six to about eight hours after the sorbitol enters the rumen. In one particularly preferred formulation, the feed composition includes about 13 weight percent alfalfa haylage, about 13 weight percent alfalfa hay, about 26 weight percent corn silage, about 19 weight percent cracked corn, about 8 weight percent Peak Plus® 37 feed formula, about 10.4 weight percent Fresh Tran Plus® formula feed, about 4.5 weight percent Condition Plus® feed formula, and about 4.7 weight percent QLF® 4-19 formula feed, based upon the dry matter weight of the feed composition.

When the feed composition is based upon a combination of (1) forage and (2) beans, grains, bean-derivatives, and/or grain derivatives, it is believed that the feed composition will be adequate to permit at least as much as about 50 weight percent of the sugar alcohol, based upon the total amount of sugar alcohol orally fed to the ruminant, to pass through the rumen of the ruminant and into the abomasum of the ruminant within about six to about eight hours after the sugar alcohol enters the rumen, when using sorbitol as the sugar alcohol, so long as the feed composition includes up to about 50 weight percent of forage and about 50 weight percent or more of beans, grains, bean derivatives, grain derivatives and any combination of these, based upon the total dry matter weight of the feed composition. Some non-exhaustive examples of suitable forages are alfalfa hay and alfalfa haylage. Some non-exhaustive examples of suitable beans and grains include corn, soybeans, and milo. Some non-exhaustive examples of suitable bean and grain derivatives include silage, syrup, meal, and oils derived from beans and/or grain. The formulation of the feed composition is preferably adequate to permit at least as much as about 50 weight percent of the sugar alcohol, based upon the total amount of sugar alcohol orally fed to the ruminant, to pass through the rumen of the ruminant and into the abomasum of the ruminant within about six to about eight hours after the sugar alcohol enters the rumen, when using sorbitol as the sugar alcohol and, more preferably, when using any of the listed sugar alcohols as the sugar alcohol.

The preferred sorbitol form of the sugar alcohol may generally be orally fed to the ruminants at the rate of about 100 grams, or less, of sorbitol per ruminant per day, so long as some sorbitol is fed to the ruminant daily. In one preferred form, sorbitol is fed to the ruminants at the rate of about 50 grams of sorbitol to about 100 grams of sorbitol per ruminant per day. In one particularly preferred embodiment, sorbitol is fed to the ruminants at the rate of about 50 grams of sorbitol per ruminant per day.

The sugar alcohol may be included as part of the feed composition Alternatively, the sugar alcohol may be added to the feed composition as a post-treatment, after the feed composition has been placed in the feed trough of the ruminants that are being fed in accordance with the present invention. After top dressing the sugar alcohol onto the feed composition, it has been found beneficial to periodically stir the feed composition in front of the ruminants being fed. This stirring tends to draw the attention of the ruminants to the feed composition and thereby tends to cause the ruminants to eat some additional amount of the feed composition that includes or has been top dressed with sugar alcohol in accordance with the present invention.

Various analytical techniques are employed herein. An explanation of these techniques follows. All values presented in this document for a particular parameter, such as weight percent true protein, weight percent fat, weight percent lactose, weight percent non-protein nitrogen, and weight percent total solids, are based on the "as is" sample and are therefore on a "wet basis", unless otherwise specified herein.

Property Determination and Characterization Techniques

To determine the dry matter weight (or dry matter basis or dry basis) of a particular sample, the sample is first weighed. The weighed sample is then dried in an oven at a temperature that is adequate to drive off moisture from the sample without degrading the sample components, such as a temperature ranging from about 100° C. to about 110° C. The oven drying is continued until the weight of the dried sample remains constant, despite additional oven drying.

To determine the weight percent total solids, wet basis, in a sample, the actual weight of total solids is determined by analyzing the sample in accordance with Method #925.23 (33.2.09) of *Official Methods of Analysis*, Association of Official Analytical Chemists (AOAC) (16th Ed., 1995). The weight percent total solids, wet basis, is then calculated by dividing the actual weight of total solids by the actual weight of the sample.

To determine the percent of total protein, wet basis, in a sample, the actual weight of total protein is determined in accordance with Method #991.20 (33.2.11) of *Official Methods of Analysis*, Association of Official Analytical Chemists (AOAC) (16th Ed., 1995). The value determined by the above method yields "total Kjeldahl nitrogen," which is equivalent to "total protein" since the above method incorporates a factor that accounts for the average amount of nitrogen in protein. Since any and all total Kjeldahl nitrogen determinations presented herein are based on the above method, the terms "total Kjeldahl nitrogen" and "total protein" are used interchangeably herein. Furthermore, those skilled in the art will recognize that the term "total Kjeldahl nitrogen" is generally used in the art to mean "total protein" with the understanding that the factor has been applied. The weight percent total protein, wet basis, is calculated by dividing the actual weight of total protein by the actual weight of the sample.

The weight percent of true protein, wet basis, for a particular sample is calculated after first determining the wet basis weight percent of total Kjeldahl nitrogen and the wet basis weight percent of non-protein nitrogen in the sample. The wet basis weight percent of total Kjeldahl nitrogen in the sample is determined using the method referenced above. The wet basis weight percent of non-protein nitrogen (NPN) in the sample is determined in accordance with Method #991.21 (33.2.12) of *Official Methods of Analysis*, Association of Official Analytical Chemists (AOAC) (16th Ed., 1995). The weight percent of true protein, wet basis, in the sample is then determined by subtracting the wet basis weight percent of non-protein nitrogen in the sample from the wet basis weight percent of total Kjeldahl nitrogen in the sample.

To determine the weight percent lactose, wet basis, in a liquid sample, the weight of the liquid sample is first determined. The actual weight of lactose in the liquid sample may then be determined using analysis kit number 176-303, that is available from Boehringer-Mannheim of Indianapolis, Ind. in accordance with the procedural instructions included with analysis kit number 176-303. The weight percent lactose, wet basis, in the liquid sample is then calculated by dividing the actual weight of lactose in the liquid sample by the actual weight of the liquid sample.

To determine the weight percent fat, wet basis, in a sample, the actual weight of fat in the sample is determined in accordance with Method #974.09 (33.7.18) of *Official Methods of Analysis*, Association of Official Analytical Chemists (AOAC) (16th Ed., 1995). The weight percent fat, wet basis, is then calculated by dividing the actual weight of fat in the sample by the actual weight of the sample.

The present invention is more particularly described in the following examples which are intended as illustrations only since numerous modifications and variations within the scope of the present invention will be apparent to those skilled in the art.

EXAMPLES

Example 1

This example demonstrates the effect of orally feeding lactating cows sorbitol at the rate of about 100 grams of sorbitol per day per cow. In this example, twenty Holstein cows averaging about thirty days in milk each, and thus in early lactation, were arranged in a randomized complete block design. Ten of the twenty cows were orally fed a control ration, and the other ten cows were orally fed a test ration that consisted of the control ration plus about 100 grams of sorbitol per day per cow.

The cows were blocked by parity milk production, based upon the level of milk production by individual cows, after being in milk for fifteen to twenty days. After being blocked by parity milk production, the cows were randomly allotted to the control ration feeding or to the test ration feeding. The components of the control ration used in this example are shown in Table 1:

TABLE 1

| COMPONENTS | WEIGHT PERCENT (DRY BASIS) |
|---|---|
| alfalfa haylage | 13.0 |
| alfalfa hay | 13.0 |
| corn silage | 26.0 |
| corn, cracked | 18.8 |
| Peak Plus ® 37 formula feed | 8.0 |
| Fresh Tran Plus ® formula feed | 10.4 |
| Condition Plus ® formula feed | 4.5 |
| QLF ® 4-19 formula feed | 4.7 |
| other minor ingredients | 1.6 |

The ingredient list for the control ration having the composition of Table 1 is broken down in Table 2 below:

TABLE 2

| COMPONENT | WEIGHT PERCENT (DRY BASIS) |
|---|---|
| alfalfa haylage | 13.0 |
| alfalfa hay | 13.0 |
| corn silage | 26.0 |
| corn, cracked | 18.8 |
| QLF ® 4-19 formula feed | 4.7 |
| whole cotton seed | 4.2* |
| 48 wt. % protein soybean meal | 7.8* |
| wheat midds | 1.9* |
| soy hulls | 1.1* |
| SoyPass ™ protein-modified soybean meal | 2.6* |
| dried distiller's grain with solubles | 1.9* |
| molasses | 0.5* |
| Megalac ® fat base | 0.9* |
| other minor ingredients | 3.7** |

*derived from Peak Plus ® 37 formula feed, Fresh Tran Plus ® formula feed, and/or Condition Plus ® formula feed
**derived from Peak Plus ® 37 formula feed, Fresh Tran Plus ® formula feed, and/or Condition Plus ® formula feed and from other minor ingredients listed in Table 1

Table 3 includes a summary of particular nutrients present in the control ration:

TABLE 3

| NUTRIENT | WEIGHT PERCENT (DRY BASIS) |
| --- | --- |
| crude protein | 18.1 |
| acid detergent soluble fiber (ADF) | 18.9 |
| neutral detergent soluble fiber (NDF) | 27.5 |
| fat | 6.0 |
| calcium | 1.05 |
| phosphorous | 0.52 |

The control ration was placed in the feeding troughs of the cattle once daily in the morning. When the test ration was to be provided to the test cattle, sorbitol was top dressed and lightly mixed into the control ration in the feeding trough of each cow being supplied with the test ration dosage of about 100 grams of sorbitol per cow per day, about one hour after the control ration was placed in the feeding trough. Then, the control ration and the test ration were lightly mixed in front of the cows six times per day to encourage additional feed ingestion by the cattle.

Leftover rations from the previous day's feeding were collected and weighed from each feeding trough prior to feeding the test cattle the next day. The cows received a sufficient amount of the control ration to ensure that at least about ten weight percent, based upon the amount of control ration provided at the beginning of each day, remained per day for each test cow. The amount of sorbitol that was top dressed in the control ration to form the test ration was adjusted upward to account for the excess of control ration provided to ensure that the cows ingested the test ration dosage of about 100 grams of sorbitol per cow per day. Feed refusals were measured daily, and water was supplied ad libitum. Each test cow received routine care and management consistent with appropriate recommendations in the *Guide for the Care and Use of Agricultural Animals in Agricultural Research and Teaching* (1st edition, March 1983).

Each cow was milked three times daily and the weight of produced milk was recorded at each milking. The milk was sampled once per day (⅓ of the sample volume from each milking) and was analyzed for protein, fat, lactose, and total solids, in accordance with the property determination and characterization techniques presented above.

The milk production and milk component data was analyzed using the general linear model (GLM) statistical procedure of SAS® statistical analysis software for a randomized, complete block design that included both the particular feed regimen and the week of the test period in the model statement. The SAS® statistical analysis software is available from SAS Institute, Inc. of Cary, N.C. Additionally, all data was analyzed to determine the mean of the data for each variable under consideration over the entire experimental period.

Statistical analysis was completed for the dry matter intake, milk production amount, and milk composition parameters. The dry matter intake and the milk production rate data was covariately adjusted using pre-trial milk weights. Covariate adjustment entails the creation of a statistical adjustment factor, considering the rate of milk production of each individual cow prior to any experimental feeding, that yields a standard base line for dry matter intake and milk production rate for the test cattle, and thereby statistically accounts for any variations in dry matter intake and milk production rate between different cattle prior to feeding in accordance with this example.

Additionally, the PDiff function of the GLM statistical procedure was used to characterize the mean value by providing a Probability value (P) for comparing between the mean values of the group fed the control ration and the mean values of the group fed the test ration, for particular test parameters or variables. The probability value, P, is a measure of the statistical probability that the differing parameter values between the cattle fed the control ration control cattle and the cattle fed the test ration may be explained by the difference between not feeding sorbitol versus feeding sorbitol.

A P value of 0.10 means that 10 times out of 100 the results can be explained by factors other than the feeding of sorbitol versus the lack of sorbitol feeding. Likewise, a P value of 0.77 means that 77 times out of 100, the difference in value between the control group and the sorbitol-fed group may be explained by factors other than the feeding of sorbitol versus the lack of sorbitol feeding. For purposes of comparing data in this document, P values of 0.10, or lower, are considered to be statistically significant. Thus, where a P value of 0.10 or less is returned for particular results, it is assumed that the differing results are fully explained by the test regimen, i.e.: the feeding of sorbitol versus the lack of sorbitol feeding.

The mean of the dry matter intake and of the milk production for the cattle fed the control ration and for the group fed the test ration over the entire twenty-eight day test period are provided in Table 4.

TABLE 4

| PRODUCTION PARAMETER | CONTROL RATION* | TEST RATION** | PROBABILITY VALUE (P) |
| --- | --- | --- | --- |
| Dry Matter Intake (pounds/day/cow) | 47.2 | 45.6 | 0.54 |
| Milk Production (pounds/day/cow) | 88.9 | 93.5 | 0.02 |

*The control ration had the composition shown in Table 1.
**about 100 grams of sorbitol per day per cow mixed with control ration.

Additionally, the dry matter intake and the milk production rate over the four week test period for the cattle fed the control ration and for the cattle fed the test ration are graphically presented in FIGS. 1 and 2, respectively. The dry matter intake and the milk production rate data points included in FIGS. 1 and 2 are mean values for the cattle fed the control ration and for the cattle fed the test ration, respectively, at the end of each week of the four week test period.

The dry matter intake data presented in FIG. 1 illustrates that the cattle fed the control ration had a higher daily dry matter intake rate than the cattle fed the test ration. However, as exemplified by the probability value P of 0.54 for the dry matter intake data that is presented in Table 4 above, this difference in dry matter intake between the cattle fed the control ration and the cattle fed the test ration is statistically insignificant, and is thought to be linked most likely to suppressed dry matter intake of one or two of the test cows that is unrelated to the sorbitol feeding regimen.

The milk production data that is presented in FIG. 2 demonstrates that for each weekly data point, there was a significant increase in daily milk production for the test cows that were fed sorbitol versus the control cows that were not fed sorbitol. This difference in milk production rates that is exhibited in FIG. 2 is, as exemplified by the probability value P of only 0.02 that is presented in Table 4, directly caused by the sorbitol feeding of the test cows. The probability value P of 0.02 means that there is 98% confidence that the sorbitol feeding regimen in the test cows caused the significant increase in the milk production rate of the test cows, versus the milk production rate of the control cows. The data of Table 4 clearly shows that there was a mean increase of about 4.6 pounds per day per cow of milk production for the test cows, versus the control cows, over the four week test period.

Example 2

This example demonstrates the differential effect of orally feeding lactating cows a control ration, a first test ration formed of the control ration and sorbitol that was orally fed to the cattle at the rate of about 50 grams of sorbitol per day per cow, and a second test ration-formed of the control ration and sorbitol that was orally fed to the cattle at the rate of about 100 grams of sorbitol per day per cow. In this example, fifteen Holstein cows (nine multiparous and six primiparous) averaging about sixty-five days in milk each, and thus in early lactation, were arranged in a 3×3 Latin square design, also known as the switch back design, that was replicated five times. Each cow was randomly allotted to the control ration treatment, to the first test ration treatment, or to the second test ration treatment.

In the 3×3 Latin square design, each cow is cycled through each treatment, namely, the control ration treatment, the first test ration treatment, and the second test ration treatment. This permits each cow to act as a control for standardizing the testing differences observed between each treatment for each cow. Sufficient time between feeding treatments (between the control ration treatment, the first ration test treatment, and the second test ration treatment) was allowed to permit normalization of each cow before being switched to a different treatment.

The cows were blocked by parity milk production, based upon the level of milk production by individual cows, after being in milk for forty-five days. After being blocked by parity milk production, the cows were randomly allotted to the control ration feeding, the first test ration feeding, or the second test ration feeding. The components of the control ration used in this example are shown in Table 5:

TABLE 5

| COMPONENTS | WEIGHT PERCENT (DRY BASIS) |
|---|---|
| alfalfa haylage | 13.0 |
| alfalfa hay | 13.0 |
| corn silage | 26.0 |
| corn, cracked | 18.8 |
| Peak Plus ® 37 formula feed | 8.0 |
| Fresh Tran Plus ® formula feed | 10.4 |
| Condition Plus ® formula feed | 4.5 |
| QLF ® 4-19 formula feed | 4.7 |
| other minor ingredients | 1.6 |

The ingredient list for the control ration having the composition of Table 5 is broken down in Table 6 below:

TABLE 6

| INGREDIENT | WEIGHT PERCENT (DRY BASIS) |
|---|---|
| alfalfa haylage | 13.0 |
| alfalfa hay | 13.0 |
| corn silage | 26.0 |
| corn, cracked | 18.8 |
| QLF ® 4-19 formula feed | 4.7 |
| whole cotton seed | 4.2* |
| 48 wt. % protein soybean meal | 7.8* |
| wheat midds | 1.9* |
| soy hulls | 1.1* |
| SoyPass ™ protein-modified soybean meal | 2.6* |
| dried distiller's grain with solubles | 1.9* |
| molasses | 0.5* |
| Megalac ® fat base | 0.9* |
| other minor ingredients | 3.7** |

*derived from Peak Plus ® 37 formula feed, Fresh Tran Plus ® formula feed, and/or Condition Plus ® formula feed
**derived from Peak Plus ® 37 formula feed, Fresh Tran Plus ® formula feed, and/or Condition Plus ® formula feed and from other minor ingredients listed in Table 5

Table 7 includes a summary of particular nutrients present in the control ration:

TABLE 7

| NUTRIENT | WEIGHT PERCENT (DRY BASIS) |
|---|---|
| crude protein | 18.1 |
| acid detergent soluble fiber (ADF) | 18.9 |
| neutral detergent soluble fiber (NDF) | 27.5 |
| fat | 6.0 |
| calcium | 1.05 |
| phosphorous | 0.52 |

The control ration was placed in the feeding troughs of the cattle once daily in the morning. When the first test ration was to be provided to the test cattle, sorbitol was top dressed and lightly mixed into the control ration in the feeding trough of each cow being supplied with the first test ration dosage of about 50 grams of sorbitol per cow per day, about one hour after the control ration was placed in the feeding trough. When the second test ration was to be provided to the test cattle, sorbitol was top dressed and lightly mixed into the control ration in the feeding trough of each cow being supplied with the second test ration dosage of about 100 grams of sorbitol per cow per day, about one hour after the control ration was placed in the feeding trough. Then, the control ration, the first test ration, and the second test ration were lightly mixed in front of the cows six times per day to encourage additional feed ingestion by the cattle.

Leftover rations from the previous day's feeding were collected and weighed from each feeding trough prior to feeding the test cattle the next day. The cows received a sufficient amount of the control ration to ensure that at least about ten weight percent, based upon the amount of control ration provided at the beginning of each day, remained per day for each test cow. The amount of sorbitol that was top dressed in the control ration to form the first test ration was adjusted upward to account for the excess of control ration provided to ensure that the cows ingested the first test ration dosage of about 50 grams of sorbitol per cow per day. Likewise, the amount of sorbitol that was top dressed in the control ration to form the second test ration was adjusted upward to account for the excess of control ration provided to ensure that the cows ingested the second test ration dosage of about 100 grams of sorbitol per cow per day. Feed refusals were measured daily, and water was supplied ad libitum. Each test cow received routine care and management consistent with appropriate recommendations in the *Guide for the Care and Use of Agricultural Animals in Agricultural Research and Teaching* (1st edition, March 1988).

Each cow was milked three times daily and the weight of produced milk was recorded at each milking. The milk was sampled once per day (⅓ of the sample volume from each milking) and was analyzed for protein, fat, lactose, and total solids, in accordance with the property determination and characterization techniques presented above.

The milk production and milk component data was analyzed using the general linear model (GLM) statistical procedure of SAS® statistical analysis software for a 3×3 Latin square design that included both the particular feed regimen and the week of the test period in the model statement. The SAS® statistical analysis software is available from SAS institute, Inc. of Cary, N.C. Data analysis based upon the standard GLM procedures using the SAS® statistical analysis system incorporated the degrees of freedom presented in Table 8 below:

Additionally, all data was analyzed to determine the mean of the data for each variable under consideration over the final two weeks of the experimental periods for the control ration treatment, for the first test ration treatment, and for the second test ration treatment. Data was not collected during the first two weeks of the four week experimental period to allow the cattle an acclimation, or adjustment, period for the different testing regimens.

Statistical analysis was completed for the dry matter intake, milk production amount, and milk composition parameters. The dry matter intake and the milk production rate data was covariately adjusted using pre-trial milk weights at 45 days in milk. Additionally, the PDiff function of the GLM statistical procedure was used to characterize the mean value by providing a Probability value (P) for comparing between the mean values of the group fed the control ration, the group fed the first test ration, and the group fed the second test ration, for particular test parameters or variables.

Production parameters for all cows (both primiparous and multiparous) are presented in Table 10 below.

TABLE 10

Production Value Means Over Last 14 Days of 28 Day Test Period (All Cows)

| PRODUCTION PARAMETER | CONTROL RATION* | FIRST TEST RATION** | SECOND TEST RATION*** | STANDARD ERROR OF THE MEAN | PROBABILITY VALUE (P) |
|---|---|---|---|---|---|
| Dry Matter Intake (pounds/day/cow) | $53.7^a$ | $55.9^b$ | $54.8^{ab}$ | 0.75 | 0.05 |
| Milk Production (pounds/day/cow) | $92.9^a$ | $97.5^b$ | $95.6^{ab}$ | 1.55 | 0.05 |
| Milk Protein (pounds/day/cow) | 2.63 | 2.77 | 2.71 | 0.06 | >0.10 |
| Lactose (pounds/day/cow) | $4.46^a$ | $4.71^b$ | $4.62^{ab}$ | 0.08 | 0.04 |
| Total Solids (pounds/day/cow) | $10.82^a$ | $11.39^b$ | $11.12^{ab}$ | 0.21 | 0.07 |

*The control ration had the composition shown in Table 5.
**about 50 grams of sorbitol per day per cow mixed with control ration.
***about 100 grams of sorbitol per day per cow mixed with control ration.
$^{ab}$Means within the same row with different superscripts differ at the probability value (P) that is indicated

TABLE 8

| SOURCE | DEGREES OF FREEDOM |
|---|---|
| Block | 4 |
| Animal (block) | 12 |
| Period (block) | 12 |
| Treatment | 2 |
| Error | 28 |
| ERROR | 44 |

Individual squares of the 3×3 Latin square design were analyzed using the degrees of freedom presented in Table 9 below:

TABLE 9

| SOURCE | DEGREES OF FREEDOM |
|---|---|
| Animal (block) | 2 |
| Period (block) | 2 |
| Treatment | 2 |
| Error | 20 |
| ERROR | 26 |

The data of Table 10 illustrates that there was an increase in both the dry matter intake rate and the milk production rate for cows receiving the first test ration (about 50 grams of sorbitol per day per cow) and for cows receiving the second test ration (about 100 grams of sorbitol per cow per day) versus the cows fed the control ration. Both the dry matter intake rate increase and the milk production rate increase are attributable to the sorbitol feeding regimen, since the probability value, P, is only 0.05 for both the dry matter intake data and for the milk production data. One surprising observation is that the lower sorbitol administration rate of the first test ration treatment, as compared to the higher sorbitol administration rate of the second test ration treatment, caused both the dry matter intake rate and the milk production rate to increase by a numerically larger amount over the dry matter intake rate and the milk production rate for cattle fed only the control ration.

It is additionally observed that the cows receiving the first test ration treatment of about 50 grams of sorbitol per day improved their milk production rate by 4.6 pounds per day per cow, versus cows fed only the control ration, which is the same milk production increase of the cows fed about 100 grams of sorbitol in the testing of Example 1. On the other hand, the cows receiving the second test ration treatment of about 100 grams of sorbitol per day in Example 2 improved their milk production rate by only 2.7 pounds per day per cow, versus cows fed only the control ration, which is less than the milk production increase of 4.6 pounds per day per cow for the cows fed about 100 grams of sorbitol in the testing of Example 1.

The difference in results between Examples 1 and 2, for the same feeding rate of about 100 grams of sorbitol per day, is possibly related to a transitional feeding period that was used in Example 2, but not in Example 1. Specifically, the cows used in Example 2 were fed the test ration for a two week transitional period before any samples were collected. On the other hand, in the testing of Example 1, the cows were fed sorbitol for a four week period and the test data in Example 1 is based upon samples collected over each week of the four week test period with no transition period prior to sampling. The difference in results between Examples 1 and 2, for the same feeding rate of about 100 grams of sorbitol per day, may also be related to "animal to animal" experimental variations that are sometimes encountered during dairy cattle trials. Animal to animal variations occur, on average, in about five percent of the dairy cattle herd during trials and testing. Such animal to animal variations are believed to be caused by a variety of factors that are not directly controllable, such as reproductive system cycles, viruses and other illnesses, immune system variations, and random types of shock to the animal.

The important observation from Table 10 is that both the 50 gram per day sorbitol feeding regimen and the 100 gram per day sorbitol feeding regimen produced increases in milk production, versus the milk production of cows fed only the control ration. However, on the basis of economics, the 50 gram per day sorbitol feeding regimen produced a better result than the 100 gram per day sorbitol feeding regimen, since the 50 gram per day sorbitol feeding regimen actually increased milk production over the control ration feeding regimen by a numerically higher amount than the 100 gram per day sorbitol feeding regimen.

One final observation with respect to the data of Table 10 is that both the cows fed about 50 grams of sorbitol per day and the cows fed about 100 grams of sorbitol per day showed statistically significant ($P \leq 0.10$) increases in the pounds of lactose per day per cow in the produced milk and in the pounds of total solids per day per cow in the produced milk. However, the differences in the production of these two milk components are believed to be primarily caused by the higher milk production rate, and not by a statistically significant higher percentage of lactose or total solids in the produced milk.

Production parameters for the primiparous cows used in Example 2 are presented in Table 11 below:

TABLE 11

| | Production Value Means Over Last 14 Days of 28 Day Test Period (Primiparous Cows Only) | | | | |
|---|---|---|---|---|---|
| PRODUCTION PARAMETER | CONTROL RATION* | FIRST TEST RATION** | SECOND TEST RATION*** | STANDARD ERROR OF THE MEAN | PROBABILITY VALUE (P) |
| Dry Matter Intake (pounds/day/cow) | 44.0 | 44.7 | 43.5 | 0.82 | >0.10 |
| Milk Production (pounds/day/cow) | 79.5 | 81.8 | 81.2 | 1.18 | >0.10 |
| Milk Protein (pounds/day/cow) | 2.18 | 2.20 | 2.16 | 0.05 | >0.10 |
| Lactose (pounds/day/cow) | 3.85 | 3.99 | 3.95 | 0.06 | >0.10 |
| Total Solids (sounds/day/cow) | 9.23 | 9.63 | 9.62 | 0.21 | >0.10 |

*The control ration had the composition shown in Table 5.
**about 50 grams of sorbitol per day per cow mixed with control ration.
***about 100 grams of sorbitol per day per cow mixed with control ration.

The changes in Table 11 of the values for particular production parameters for the primiparous cows are not statistically different as between the first test ration treatment and the control treatment or as between the second test ration treatment and the control treatment, since P is greater than 0.10 for each of the production parameters monitored. This demonstrates that the primiparous cows did not contribute, statistically speaking, to the increases in milk production rate, dry matter intake rate, or milk component production rate shown in Table 10 which reflects overall results for all cows, both primiparous and multiparous. This is not unexpected since primiparous cows typically show more cow to cow variation of milk production and milk component production parameters than do multiparous cows.

The production parameters for the multiparous cows that were tested in Example 2 are presented in Table 12:

TABLE 12

Production Value Means Over Last 14 days of 28 Day Test Period
(Multiparous Cows Only)

| PRODUCTION PARAMETER | CONTROL RATION* | FIRST TEST RATION** | SECOND TEST RATION*** | STANDARD ERROR OF THE MEAN | PROBABILITY VALUE (P) |
|---|---|---|---|---|---|
| Dry Matter Intake (pounds/day/cow) | 60.2$^a$ | 63.3$^b$ | 62.3$^{ab}$ | 1.16 | 0.09 |
| Milk Production (pounds/day/cow) | 101.9$^a$ | 108.0$^b$ | 105.3$^{ab}$ | 2.15 | 0.07 |
| Milk Protein (pounds/day/cow) | 2.93$^a$ | 3.15$^b$ | 3.07$^{ab}$ | 0.08 | 0.08 |
| Lactose (pounds/day/cow) | 4.86$^a$ | 5.19$^b$ | 5.07$^{ab}$ | 0.12 | 0.07 |
| Total Solids (pounds/day/cow) | 11.87 | 12.57 | 12.13 | 0.29 | >0.10 |

*The control ration had the composition shown in Table 2.
**about 50 grams of sorbitol per day per cow mixed with control ration.
***about 100 grams of sorbitol per day per cow mixed with control ration.
$^{ab}$Means within the same row with different superscripts differ at the probability value (P) that is indicated The data presented in Table 12 for the multiparous cows continues to demonstrate many of the production parameter changes observed in the "all cow" testing results of Table 10. For example, the dry matter intake rate and the milk production rate increased, as compared to the dry matter intake rate and milk production rate for cattle fed the control ration, for both the cows fed about 50 grams of sorbitol per day and for the cows fed about 100 grams of sorbitol per day. However, similar to the observation noted above with respect to the "all cow" data of Table 10, the multiparous cows fed about 50 grams of sorbitol per day showed larger numerical increases in both the dry matter intake and milk production rates over the cattle fed the control ration, as compared to the multiparous cows fed about 100 grams of sorbitol per day.

Additionally, for the multiparous cows, both the milk protein production rate and the lactose production rate in the produced milk increased for both the 50 gram per day sorbitol treatment and the 100 gram per day per cow sorbitol treatment versus the control ration treatment. Again, the production rates of milk protein and lactose increased by a numerically larger amount for the cows fed about 50 grams of sorbitol per day, versus those fed at the higher rate of about 100 grams of sorbitol per day. Again, the increases in milk component production rates for the sorbitol treatments, versus the control treatment, are believed to be caused by the higher milk production rates, rather than by higher percentages of components in the produced milk.

Finally, production parameters for individual blocks of cows fed the control ration, the first test ration, and the second test ration are presented in Table 13 that follows.

TABLE 13

Production Value Means For Individual
Blocks Over The Last 14 Days Of The 28 Day Test Period

| PRODUCTION PARAMETER | CONTROL RATION* | FIRST TEST RATION** | SECOND TEST RATION*** | STANDARD ERROR OF THE MEAN | PROBABILITY VALUE (P) |
|---|---|---|---|---|---|
| Dry Matter Intake (pounds/day/cow) | | | | | |
| Block 1 | 45.0 | 44.2 | 44.4 | 0.99 | >0.10 |
| Block 2 | 42.9$^a$ | 45.3$^b$ | 42.6$^{ab}$ | 1.35 | 0.04 |
| Block 3 | 54.4$^a$ | 60.7$^b$ | 60.1$^{ab}$ | 1.55 | 0.10 |
| Block 4 | 61.0 | 62.6 | 61.2 | 0.50 | >0.10 |
| Block 5 | 65.1 | 66.6 | 65.8 | 1.76 | >0.10 |
| Milk Production (pounds/day/cow) | | | | | |
| Block 1 | 83.7 | 85.5 | 85.2 | 2.73 | >0.10 |
| Block 2 | 75.3$^a$ | 78.0$^b$ | 77.1$^{ab}$ | 0.67 | 0.10 |
| Block 3 | 89.0 | 98.8 | 99.0 | 4.70 | 0.28 |
| Block 4 | 97.6$^a$ | 102.9$^b$ | 95.9$^{ab}$ | 1.07 | 0.07 |
| Block 5 | 119.1$^a$ | 122.4$^b$ | 121.0$^{ab}$ | 0.76 | 0.10 |
| Milk Protein (pounds/day/cow) | | | | | |
| Block 1 | 2.23 | 2.22 | 2.19 | 0.10 | >0.10 |
| Block 2 | 2.13 | 2.18 | 2.12 | 0.06 | >0.10 |
| Block 3 | 2.62 | 2.89 | 2.85 | 0.16 | >0.10 |
| Block 4 | 2.83$^a$ | 3.18$^b$ | 3.01$^{ab}$ | 0.08 | 0.08 |
| Block 5 | 3.35 | 3.39 | 3.36 | 0.03 | >0.10 |

TABLE 13-continued

Production Value Means For Individual
Blocks Over The Last 14 Days Of The 28 Day Test Period

| PRODUCTION PARAMETER | CONTROL RATION* | FIRST TEST RATION** | SECOND TEST RATION*** | STANDARD ERROR OF THE MEAN | PROBABILITY VALUE (P) |
|---|---|---|---|---|---|
| Lactose (pounds/day/cow) | | | | | |
| Block 1 | 3.99 | 4.10 | 4.07 | 0.04 | >0.10 |
| Block 2 | $3.72^a$ | $3.89^b$ | $3.82^{ab}$ | 0.04 | 0.07 |
| Block 3 | 4.32 | 4.84 | 4.86 | 0.24 | >0.10 |
| Block 4 | $4.56^a$ | $4.88^b$ | $4.57^{ab}$ | 0.06 | 0.06 |
| Block 5 | $5.70^a$ | $5.86^b$ | $5.78^{ab}$ | 0.03 | 0.05 |
| Total Solids (pounds/day/cow) | | | | | |
| Block 1 | 9.51 | 9.77 | 9.94 | 0.41 | >0.10 |
| Block 2 | 8.95 | 9.48 | 9.29 | 0.15 | >0.10 |
| Block 3 | 10.70 | 11.53 | 11.62 | 0.64 | >0.10 |
| Block 4 | $11.46^a$ | $12.35^b$ | $11.01^{ab}$ | 0.30 | 0.09 |
| Block 5 | 13.46 | 13.83 | 13.78 | 0.28 | >0.10 |

*The control ration had the composition shown in Table 5.
**about 50 grams of sorbitol per day per cow mixed with control ration.
***about 100 grams of sorbitol per day per cow mixed with control ration.
$^{ab}$Means within the same row with different superscripts differ at the probability value (P) that is indicated Consistent with the increased dry matter intake rate data and the increased milk production rate data of Table 10, most blocks presented in Table 13 show statistically significant (P≤0.10) increases in both the dry matter intake rate and the milk production rate. Similar comments apply with respect to the lactose production rate, though the increases in lactose production rate are believed primarily attributable to the increase in milk production rate for the cows given the first test ration and the second test ration.

Although the present invention has been described with reference to preferred embodiments, workers skilled in the art will recognize that changes may be made in form and detail without departing from the spirit and scope of the invention.

The invention claimed is:

1. A method of increasing milk production in a lactating ruminant without statistically increasing dry matter intake, the method comprising:
   top dressing a feed with sugar alcohol, the feed comprising forage or one or more non-forage feed components, the sugar alcohol comprising one or more of adonitol, allitol, altritol, arabinitol, dulcitol, erythritol, galaxitol, glucitol, iditol, inositol, isomalt, lactitol, maltitol, mannitol, perseitol, ribitol, rhamnitol, sorbitol, threitol or xylitol,
   feeding the lactating ruminant the top-dressed feed in a feed ration; and
   observing the lactating ruminant fed the feed ration exhibits increased milk production without statistically increasing dry matter intake.

2. The method of claim 1, wherein the sugar alcohol comprises at least sorbitol.

3. The method of claim 1, wherein the feed includes the forage, the forage comprising one or more of haylage, hay or silage.

4. The method of claim 1, wherein the feed includes the non-forage feed components, the non-forage feed components comprising one or more of a grain, a bean, a grain product or a bean product.

5. The method of claim 4, wherein at least a portion of the non-forage feed components are contained in a formula feed.

6. The method of claim 1, wherein the sugar alcohol is in an aqueous mixture.

7. The method of claim 1, wherein the sugar alcohol comprises one or more of crystalline sugar alcohol or sugar alcohol syrup.

* * * * *